(12) United States Patent
Sweeney et al.

(10) Patent No.: US 12,296,133 B2
(45) Date of Patent: May 13, 2025

(54) FLUID DELIVERY DEVICE AND BONE SCREW

(71) Applicant: Spinal Generations, LLC, Mokena, IL (US)

(72) Inventors: Patrick J. Sweeney, Flossmoor, IL (US); Matthew V. Leyden, St. Paul, MN (US)

(73) Assignee: SPINAL GENERATIONS, LLC, Mokena, IL (US)

( * ) Notice: Subject to any disclaimer, the term of this patent is extended or adjusted under 35 U.S.C. 154(b) by 1401 days.

(21) Appl. No.: 16/601,169

(22) Filed: Oct. 14, 2019

(65) Prior Publication Data

US 2020/0038646 A1    Feb. 6, 2020

Related U.S. Application Data

(63) Continuation-in-part of application No. 29/667,131, filed on Oct. 18, 2018, now Pat. No. Des. 863,049, which is a continuation of application No. 29/597,124, filed on Mar. 14, 2017, now Pat. No. Des. 831,476.

(51) Int. Cl.
*A61M 39/02* (2006.01)
*A61B 17/86* (2006.01)
*A61B 17/88* (2006.01)
*A61B 17/56* (2006.01)
*A61M 39/10* (2006.01)

(52) U.S. Cl.
CPC ....... *A61M 39/0247* (2013.01); *A61B 17/864* (2013.01); *A61B 17/8875* (2013.01); *A61B 2017/561* (2013.01); *A61B 2017/564* (2013.01); *A61M 2039/0205* (2013.01); *A61M 2039/025* (2013.01); *A61M 2039/0273* (2013.01); *A61M 2039/1038* (2013.01); *A61M 2210/02* (2013.01)

(58) Field of Classification Search
CPC ........ A61M 39/0247; A61M 2039/025; A61M 2039/0205; A61M 2039/0223; A61M 2039/0261; A61M 2039/0276; A61M 2039/1038; A61M 2210/02; A61B 17/3472; A61B 17/864; A61B 17/8816; A61B 17/8875; A61B 17/8877
See application file for complete search history.

(56) References Cited

U.S. PATENT DOCUMENTS

D242,428 S    11/1976   Morris
D358,212 S     5/1995   Sullivan
(Continued)

*Primary Examiner* — Laura A Bouchelle
*Assistant Examiner* — Sarah Dympna Grasmeder
(74) *Attorney, Agent, or Firm* — FOLEY & LARDNER LLP

(57) ABSTRACT

A delivery device for delivering substance to bone includes a luer portion configured to be detachably coupled to a bit driver, the luer portion having a luer thread. A bit portion is rigidly coupled the luer portion, and the bit portion is configured to accommodate the bit driver. A fluted portion is rigidly coupled to the bit portion, the fluted portion comprising a flute, the flute configured to create a hole in the bone. A conduit extends through the luer portion and the bit portion, at least partially through the fluted portion. The flute defines an aperture extending from the conduit entirely through the flute, and the aperture is configured to allow a substance to pass therethrough.

16 Claims, 1 Drawing Sheet

(56) References Cited

U.S. PATENT DOCUMENTS

| | | |
|---|---|---|
| D366,115 S | 1/1996 | Sullivan |
| D441,448 S | 5/2001 | Kumar |
| D574,958 S | 8/2008 | Schendel et al. |
| D614,941 S | 5/2010 | Murphy |
| D706,893 S | 6/2014 | Diederich |
| D744,106 S | 11/2015 | Voudouris |
| D773,926 S | 12/2016 | Sweeney et al. |
| D801,796 S | 11/2017 | Sweeney et al. |
| D803,038 S | 11/2017 | Baker et al. |
| D803,039 S | 11/2017 | Karlsson |
| D828,153 S | 9/2018 | Sato |
| D830,820 S | 10/2018 | Sweeney |
| D831,475 S | 10/2018 | Sweeney et al. |
| D831,476 S | 10/2018 | Sweeney et al. |
| D836,976 S | 1/2019 | Reese et al. |
| D837,047 S | 1/2019 | Lin |
| 2002/0123752 A1* | 9/2002 | Schultheiss ........ A61B 17/8685 606/92 |
| 2005/0107800 A1* | 5/2005 | Frankel .............. A61B 17/1655 606/92 |
| 2007/0142842 A1* | 6/2007 | Krueger ............. A61B 17/8819 606/92 |
| 2010/0063550 A1* | 3/2010 | Felix .................... A61B 17/866 606/301 |
| 2011/0056166 A1 | 3/2011 | Bartlett |
| 2011/0257691 A1 | 10/2011 | Sutterlin et al. |
| 2014/0236242 A1* | 8/2014 | Robinson ........... A61B 17/8605 606/279 |
| 2015/0272646 A1* | 10/2015 | Russell .............. A61B 17/8811 606/93 |
| 2016/0213413 A1* | 7/2016 | Hientzsch .......... A61B 17/8635 |
| 2016/0325072 A1* | 11/2016 | Shevgoor .......... A61M 25/0015 |
| 2017/0209129 A1* | 7/2017 | Fagundes ........... A61B 17/3472 |

* cited by examiner

FLUID DELIVERY DEVICE AND BONE SCREW

CROSS-REFERENCE TO RELATED PATENT APPLICATIONS

This application is a Continuation-in-Part of U.S. Design patent application Ser. No. 29/667,131, filed on Oct. 23, 2018, which is a Continuation of U.S. Design application Ser. No. 29/597,124, filed on Mar. 14, 2017, each of which are hereby incorporated by reference in their entirety.

BACKGROUND

The present invention relates generally to the field of surgical tools and implements, and more particularly to delivery devices for use in surgical and related healthcare settings. More particularly, the present invention concerns devices and methods for delivering substances to the interior or exterior of fractured or otherwise injured bones, especially to the fracture interface thereof. The present invention also relates to devices and methods for removing materials from the interior of bone. The present invention further relates to devices and methods of bone fixation.

A delivery device provides for delivery of a fluid to a bone, such as bone void filler, bone cement, or an antibiotic. A complication associated with the use of some delivery devices is insufficient engagement between the device and the bone, which causes the possibility of extravasation, or leakage of the fluid into the surrounding tissue.

As such, some delivery devices are also configured with features to allow for fixation of the delivery device to the bone or serve as fixation devices as well as delivery devices. Fixation devices, such as bone screws, are used in many surgical procedures carried out in a healthcare setting. For example, in orthopedic surgery, bone screws are often used to secure an intramedullary nail in a fractured long bone, or to secure a plate to other fractured bones. A bone screw stabilizes the fracture to facilitate healing of the fracture.

A fixation device, such as a bone screw, is typically made of stainless steel, titanium, or other strong metals and are designed to remain in the body for extended periods of time, though some are designed with other materials and/or designed to be removed or dissolved within the body. Depending on the desired function of a bone screw, the bone screw may include one of a variety of tips and thread designs. In addition, bone screws are available in a variety of lengths and diameters depending on the location of the fracture and the relative size of the bone. Typically, a bone screw can be inserted into bone after a pilot hole is drilled in the bone. In some cases, a bone screw can be inserted without the use of a pilot hole.

SUMMARY OF THE INVENTION

One embodiment of the invention relates to a delivery device for delivering substance to bone includes a luer portion configured to be detachably coupled to a bit driver, the luer portion having a luer thread. A bit portion is rigidly coupled the luer portion, and the bit portion is configured to accommodate the bit driver. A fluted portion is rigidly coupled to the bit portion, the fluted portion comprising a flute, the flute configured to create a hole in the bone. A conduit extends through the luer portion and the bit portion, at least partially through the fluted portion. The flute defines an aperture extending from the conduit entirely through the flute, and the aperture is configured to allow a substance to pass therethrough.

Another embodiment of the invention relates to a method for delivering substance to bone that includes providing a delivery device. The delivery device includes a luer portion configured to be detachably coupled to a bit driver, the luer portion including a luer thread. A bit portion is rigidly coupled to the luer portion, and the bit portion is configured to accommodate the bit driver. A fluted portion is rigidly coupled to the bit portion, the fluted portion comprising a flute, the flute configured to create a hole in the bone. A conduit extends through the luer portion and the bit portion, at least partially through the fluted portion. The flute defines an aperture, the aperture extending from the conduit entirely through the flute, and the aperture is configured to allow a substance to pass through the aperture. The method further includes coupling the bit driver to the luer portion and rotating the bit driver to rotate the delivery device, wherein rotating the delivery device causes the fluted portion to drill into the bone. The method further includes delivering a substance through the conduit such that the substance flows through the aperture.

DETAILED DESCRIPTION

Figure 1:
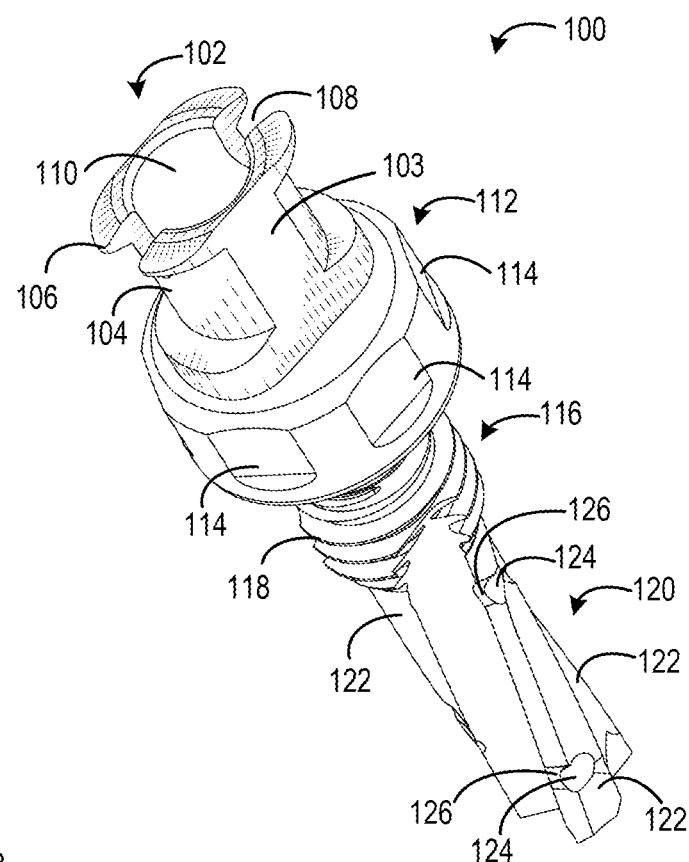
FIG. 1 is a perspective view of a delivery device, according to a preferred embodiment.
Figure 2:
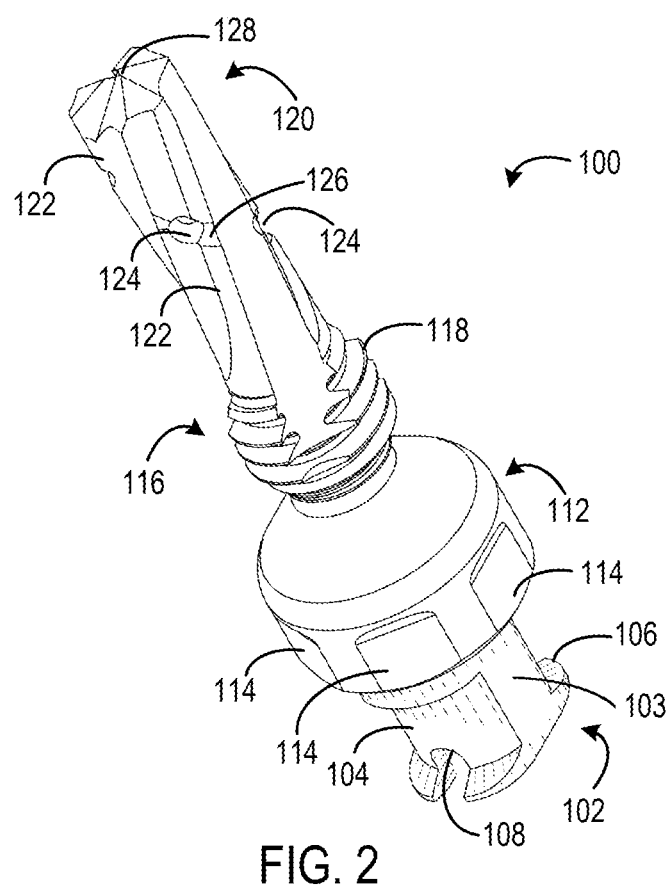
FIG. 2 is a second perspective view of the delivery device of FIG. 1.

FIGS. 1-2 are perspective views of a delivery device 100, according to a preferred embodiment. As shown, the delivery device 100 includes a luer portion 102, a bit portion 112, a threaded portion 116, and a fluted portion 120. In some embodiments, the luer portion 102, the bit portion 112, the threaded portion 116, and the fluted portion 120 may be a unitary device. In some embodiments, the luer portion 102, the bit portion 112, the threaded portion 116, and the fluted portion 120 can be individual components that are assembled during a manufacturing process. In some embodiments, at least two of the luer portion 102, the bit portion 112, the threaded portion 116, and the fluted portion 120 can be combined as a unitary component and be assembled with the remaining components during a manufacturing process.

The delivery device 100 is preferably constructed from a metal (e.g., titanium, stainless steel, etc.), a biomaterial (e.g., polylactic acid and hydroxyapatite, etc.), a plastic (e.g., thermoplastic polymers, etc.), or a composite (e.g., carbon fiber reinforced plastics, etc.) capable of withstanding forces to which the delivery device 100 will be subjected when implanted in a bone. In some embodiments, each of the luer portion 102, the bit portion 112, the threaded portion 116, and the fluted portion 120 can be constructed from the same material. In some embodiments, at least one of the luer portion 102, the bit portion 112, the threaded portion 116, and the fluted portion 120 can be constructed from different materials.

The luer portion 102 is configured to receive a peripheral substance delivery device and is shown to include a luer body 104, a luer thread 106, a cutout 108, and a conduit 110. The luer body 104 is rigidly coupled to the bit portion 112 such that the luer body 104 and the bit portion 112 cannot rotate relative to each other. As shown, the luer portion 102 is a female luer. However, in some embodiments, the luer portion 102 can be a male luer.

In some embodiments, the luer body 104 can be a standard luer (e.g., the luer body 104 conforms to the 80369-7 standard of the International Standards Organization (ISO)). In some embodiments, the luer body 104 is customized to meet the needs of the procedure. For example, the luer body 104 may be longer or shorter than specified in the ISO standard. Additionally, the luer body 104 may include a diameter that is larger or smaller than specified in the ISO standard.

The luer portion 102 is configured to be detachably coupled to a rotational bit driver. In some embodiments, the luer portion 102 may further include a flat face 103 for engaging the rotational bit driver. In some embodiments, the flat face 103 is substantially flat. The flat face 103 is configured to allow the rotational driver to rotate the delivery device 100 without slipping. In some embodiments, the luer portion 102 may include a plurality of the flat face 103. In the embodiment shown, the luer portion 102 includes a pair of the flat face 103, the pair positioned diametrically opposite around the luer portion 102.

The luer body 104 defines the conduit 110 that extends entirely through the luer portion 102. As shown, the conduit 110 conforms to the ISO standard (e.g., the conduit 110 is configured to receive a luer slip that conforms to the ISO standard). However, in some embodiments, the conduit 110 can be customized to be a different shape such that the conduit 110 can successfully receive a different connector.

The luer thread 106 extends from the luer body 104 and is configured to detachably connect to a connector that includes the appropriate mating thread (e.g., a matching male luer thread). As shown, the luer thread 106 partially extends around the circumference of the luer body 104. In some embodiments, the luer thread 106 can extend entirely around the circumference of the luer body 104.

The cutout 108 is configured to receive a rotational tool (e.g., a screwdriver, etc.) and is defined by a space in the luer thread 106 and the luer body 104. As shown, the cutout 108 is configured to receive a single-plane rotational tool (e.g., a flathead screwdriver). In some embodiments, the cutout 108 can be configured to receive a multi-plane rotational tool (e.g., a Phillips head screwdriver, a hexagonal screwdriver, etc.)

The bit portion 112 is configured to accommodate the rotational bit (e.g., a drill bit, etc.) and is shown to include cutouts 114. The bit portion 112 is rigidly coupled to the luer portion 102 and the threaded portion 116 such that there is no relative motion between the components. As shown, the bit portion 112 is a hexagonal bit. However, in some embodiments, the bit portion 112 can be any other kind of bit (e.g., an octagonal bit, a star-shaped bit, etc.). The outer diameter of the bit portion 112 is larger than the outer diameter of the luer portion 102 such that a rotational bit can fit around the luer portion 102 and engage the bit portion 112.

The cutouts 114 are located around the bit portion 112 such that the rotational bit can fit around the bit portion 112. As shown, the cutouts 114 are sections of the bit portion 112 where material has been removed. However, in some embodiments, the cutouts 114 may protrude from the bit portion 112 to receive a different kind of rotational bit. Additionally, as shown, the cutouts 114 are configured to receive a hexagonal bit. However, in some embodiments, the cutouts 114 can be configured to receive any other kind of rotational bit (e.g., an octagonal bit, a star-shaped bit, etc.).

Though not shown in FIGS. 1-2, the conduit 110 extends entirely through the bit portion 112 such that the luer portion 102 and the bit portion 112 are in fluid communication with each other.

The threaded portion 116 is configured to secure the delivery device 100 into a bone and is shown to include threads 118. The threaded portion 116 is rigidly coupled to the bit portion 112 and the fluted portion 120 such that there is no relative motion between the components.

The threads 118 extend around the circumference of the threaded portion 116 and are sized such that the major diameter of the threads 118 is larger than the outer diameter of the fluted portion 120. The threads 118 can include any type of thread design (e.g., pitch, thread angle, major diameter, minor diameter, helix angle, etc.) that effectively secures the delivery device 100 into bone.

Though not shown in FIGS. 1-2, the conduit 110 extends entirely through the threaded portion 116 such that the threaded portion 116 and the bit portion 112 are in fluid communication with each other.

The fluted portion 120 is configured to bore into bone and create a channel into which the threads 118 can secure the delivery device 100. The fluted portion 120 is rigidly coupled to the threaded portion 116 such that there is no relative motion between the components. As shown, the fluted portion 120 extends into the threaded portion 116. However, in some embodiments, the fluted portion 120 does not extend into the threaded portion 116 such that the threads 118 do not include any broken sections. The fluted portion 120 is shown to include flutes 122, apertures 124, grooves 126, and a tip 128.

Though not shown in FIGS. 1-2, the conduit 110 extends partially through the fluted portion 120 such that the fluted portion 120 and the threaded portion 116 are in fluid communication with each other.

The flutes 122 extend around the circumference of the fluted portion 120 and are configured to bore into bone and remove bone fragments. As shown, the flutes 122 are shaped like flutes from a standard drill bit. However, in some embodiments, the flutes 122 can be shaped differently such that the flutes 122 are optimized for boring into and removing bone.

The apertures 124 are defined by openings extending from an outer surface of the flutes 122 to the conduit 110 such that a fluid in the conduit 110 can be delivered from the conduit 110 and through the apertures 124 such that the fluid is external to the delivery device 100. The apertures 124 can be sized and configured based on the type of fluid being injected and the desired pressure, velocity, or volume at which the fluid should be injected. For example, when injecting a fluid with a low viscosity, the apertures 124 may be small to reduce the volume of fluid injected. As another example, when injecting a fluid with a high viscosity, the apertures 124 may be large to reduce the injection pressure. As shown, the apertures 124 are cylindrical. However, in some embodiments, the apertures 124 can be other shapes to facilitate the desired fluid injection (e.g., elliptical, square, etc.). In addition, in some embodiments the apertures 124 can have a constant cross-section extending from the conduit 110 to the outer surface of the flutes 122. In some embodiments, the apertures 124 can have a non-constant cross-section extending from the conduit 110 to the outer surface of the flutes 122.

As shown, each aperture 124 has at least one groove 126 extending axially in at least one direction, and in the embodiment shown, two grooves 126 extending in two directions, from the aperture 124 in the flutes 122. The grooves 126 facilitate fluid delivery such that the fluid is able to flow from the aperture 124, through the grooves 126, and into the spaces between each of the flutes 122 for delivery to the bone.

The tip 128 is located at the distal end of the fluted portion 120 and is configured to initiate access of the fluted portion 120 into bone. The tip 128 can include extensions of the flutes 122 such that the tip 128 can create a channel in bone and expand the channel until the flutes 122 contact the bone. The tip 128 is closed such that the conduit 110 does not extend through the tip 128.

In operation, a user may desire to fix a bone fracture using the delivery device 100. The delivery device 100 may be used to fix a bone fracture by securing bone fragments together. The delivery device 100 may also be used to fix a bone fracture by securing a plate to different bone fragments to secure the bone fragments together.

The user first determines the appropriate insertion point for the delivery device 100 and marks the insertion point on the bone. The user then secures a rotational bit to the luer portion 102, for example, by engaging with one or more flat faces 103. The rotational bit can be a hex bit such that the hex bit fits around the cutouts 114 of the bit portion 112. The rotational bit is configured to fit around the luer portion 102 such that the luer portion 102 is not damaged when the rotational bit engages the cutouts 114 on the bit portion 112. In some embodiments, the rotational bit is configured to engage the flat face 103 of the luer portion 102. In other embodiments, the luer portion 102 includes a plurality of the flat face 103, and the rotational bit is configured to engage the plurality of the flat face 103. In some embodiments, the rotational bit can be magnetized such that the luer portion 102 and/or bit portion 112 is secured in the rotational bit without additional supporting structure. In other embodiments, the user secures the luer portion 102 and/or bit portion 112 in the rotational bit by hand.

With the luer portion 102 secured in the rotational bit, the user places the tip 128 on the insertion point and rotates the rotational bit. As the rotational bit rotates, the luer portion 102 rotates, thereby rotating the delivery device 100. The tip 128 rotates against the insertion point, and the tip 128 begins to bore a hole into the bone. As the rotational bit continues to rotate, the tip 128 extends deeper into the bone until the fluted portion 120 contacts the bone. The flutes 122 remove bone as the rotational bit continues to rotate, and the delivery device 100 extends deeper into the bone.

When the threaded portion 116 reaches the surface of the bone, continuing to rotate the rotational bit drives the threads 118 into the bone to secure the delivery device 100 to the bone. Because the major diameter of the threads 118 is larger than the outer diameter of the fluted portion 120, the threads 118 extend into the bone to secure the delivery device 100 into the bone. The user can continue to rotate the rotational bit until the bit portion 112 contacts the bone. The delivery device 100 is secured in the bone and the user can stop rotating the rotational bit. In some embodiments, the user stops rotating the rotational bit upon encountering a high rotational force, indicating the bit portion 112 is in contact with the bone. In some embodiments, the rotational bit stops rotating automatically upon encountering a high rotational force. The user removes the rotational bit from the delivery device 100.

Though the delivery device 100 may be secured in the bone, additional fixation may be required to prevent the delivery device 100 from pulling out of the bone at a later time. As such, the user may choose to deliver an additional substance to further secure the delivery device 100 to the bone (e.g., bone cement). In addition, the user may choose to deliver a substance to prevent infections or other complications associated with surgery (e.g., antibiotics). The user may choose to deliver both substances to the bone. In such cases, the user can first deliver a substance to prevent infections or other complications and then deliver a substance to further secure the delivery device 100 to the bone.

To facilitate the injections, the user can fill peripheral delivery devices with the desired substances. For example, the user can fill one peripheral delivery device with an antibiotic and another peripheral delivery device with a bone cement. Both peripheral delivery devices must be compatible with the luer portion 102 such that the peripheral delivery devices can securely connect to the luer portion 102 and avoid leakage.

To inject the antibiotic, the user secures the antibiotic peripheral delivery device to the luer portion 102. The user then injects the antibiotic by forcing the antibiotic from the antibiotic peripheral delivery device and into the conduit 110. The antibiotic travels through the conduit 110, which extends through the luer portion 102, the bit portion 112, the threaded portion 116, and partially through the fluted portion 120. The antibiotic is then delivered through the apertures 124 such that the antibiotic contacts the bone. After sufficient antibiotic has been delivered, the user disconnects the antibiotic peripheral delivery device.

To inject the bone cement, the user secures the bone cement peripheral delivery device to the luer portion 102. The user then injects the bone cement by forcing the bone cement from the bone cement peripheral delivery device and into the conduit 110. The bone cement is then delivered through the conduit 110 and through the apertures 124 such that the bone cement contacts the bone. The flutes 122 serve to direct the bone cement along the delivery device 100 such that the bone cement is in contact with the bone and the delivery device 100. After sufficient bone cement has been delivered, the user disconnects the bone cement peripheral delivery device. The bone cement is then allowed to cure, thereby further securing the delivery device 100 in place.

In some embodiments, the user may desire to remove the delivery device 100 after the bone has successfully healed. To remove the delivery device 100, the user can use a screwdriver that fits within the cutout 114 and unscrew the delivery device 100. Additionally, the user can use a rotational bit to unscrew the delivery device 100.

Various exemplary embodiments of the invention are described herein. Reference is made to these examples in a non-limiting sense. They are provided to illustrate more broadly applicable aspects of the invention. Various changes may be made to the invention described and equivalents may be substituted without departing from the true spirit and scope of the invention. In addition, many modifications may be made to adapt a particular situation, material, composition of matter, process, process act(s) or step(s) to the objective(s), spirit or scope of the present invention. Further, as will be appreciated by those with skill in the art, each of the individual variations described and illustrated herein has discrete components and features which may be readily separated from or combined with the features of any of the other several embodiments without departing from the scope or spirit of the present inventions. All such modifications are intended to be within the scope of claims associated with this disclosure.

The invention includes methods that may be performed using the subject devices. The methods may include the act of providing such a suitable device. Such provision may be performed by the end user. In other words, the "providing"

act merely requires the end user obtain, access, approach, position, set-up, activate, power-up, or otherwise act to provide the requisite device in the subject method. Methods recited herein may be carried out in any order of the recited events that is logically possible, as well as in the recited order of events.

Exemplary aspects of the invention have been set forth above. As for other details of the present invention, these may be appreciated in connection with patents and publications generally known or appreciated by those with skill in the art. The same may hold true with respect to method-based aspects of the invention in terms of additional acts as commonly or logically employed by those with skill in the art.

In addition, though the invention has been described in reference to several examples optionally incorporating various features, the invention is not to be limited to that which is described or indicated as contemplated with respect to each variation of the invention. Various changes may be made to the invention described and equivalents (whether recited herein or not included for the sake of some brevity) may be substituted without departing from the true spirit and scope of the invention. In addition, where a range of values is provided, it is understood that every intervening value, between the upper and lower limit of that range and any other stated or intervening value in that stated range, is encompassed within the invention.

Also, it is contemplated that any optional feature of the inventive variations described may be set forth and claimed independently, or in combination with any one or more of the features described herein. Reference to a singular item, includes the possibility that there are plural of the same items present. More specifically, as used herein and in claims associated hereto, the singular forms "a," "an," "said," and "the" include plural referents unless specifically stated otherwise. In other words, use of the articles allow for "at least one" of the subject item in the description above as well as claims associated with this disclosure. It is further noted that such claims may be drafted to exclude any optional element. As such, this statement is intended to serve as antecedent basis for use of such exclusive terminology as "solely," "only" and the like in connection with the recitation of claim elements, or use of a "negative" limitation.

Without the use of such exclusive terminology, the term "comprising" in claims associated with this disclosure shall allow for the inclusion of any additional element—irrespective of whether a given number of elements are enumerated in such claims or the addition of a feature could be regarded as transforming the nature of an element set forth in such claims. Except as specifically defined herein, all technical and scientific terms used herein are to be given as broad a commonly understood meaning as possible while maintaining claim validity.

The breadth of the present invention is not to be limited to the examples provided and/or the subject specification, but rather only by the scope of claim language associated with this disclosure.

What is claimed is:

1. A device for delivering substance to bone, comprising:
   a luer portion configured to be detachably coupled to a bit driver, the luer portion comprising a luer thread;
   a bit portion rigidly coupled to the luer portion, the bit portion configured to accommodate the bit driver;
   a fluted portion rigidly coupled to the bit portion, the fluted portion comprising a non-threaded body comprising a flute, the flute configured to create a hole in the bone; and
   a conduit, the conduit extending entirely through the luer portion and the bit portion, and the conduit extending at least partially through the fluted portion;
      wherein the flute extends from the non-threaded body away from the conduit and defines an aperture, the aperture extending from the conduit entirely through the flute, and the aperture is configured to allow the substance to pass therethrough; and
      wherein the device further comprises a plurality of grooves extending from the aperture to facilitate flow of the substance from the aperture to the bone.

2. The device of claim 1, wherein the bit portion further comprises at least one hex bit configured to be detachably coupled to a hex bit driver.

3. The device of claim 1, wherein the luer portion defines a cutout, the cutout configured to detachably couple to a screwdriver.

4. The device of claim 1, further comprising a threaded portion rigidly coupled to the bit portion, the threaded portion comprising a thread.

5. The device of claim 4, wherein the thread is configured to secure the device into the bone.

6. The device of claim 5, further comprising a tip, the tip configured to prevent the conduit from extending entirely through the fluted portion.

7. The device of claim 6, wherein the tip is configured to cut the bone.

8. The device of claim 4, wherein at least one of the luer portion, the bit portion, the threaded portion, and the fluted portion are individual components assembled during a manufacturing process.

9. The device of claim 8, wherein the aperture is configured to allow the substance to pass through the aperture such that the substance is in contact with the bone and the fluted portion.

10. The device of claim 1, wherein the plurality of grooves extend axially from the aperture.

11. The device of claim 1, wherein the luer thread is configured to be detachably coupled to a peripheral substance delivery device.

12. The device of claim 11, wherein the peripheral substance delivery device is configured to deliver a curable material.

13. The device of claim 1, wherein the aperture is formed having a non-constant cross-sectional diameter extending from the conduit to an exterior surface of the flute.

14. The device of claim 1, wherein the plurality of grooves include a first groove and a second groove, wherein the first groove and the second groove extend axially from the aperture in opposing directions to facilitate flow of the substance from the aperture to the bone.

15. A device for delivering substance to bone, comprising:
   a luer portion configured to be detachably coupled to a bit driver, the luer portion comprising a luer thread;
   a bit portion rigidly coupled to the luer portion, the bit portion configured to accommodate the bit driver;
   a fluted portion rigidly coupled to the bit portion, the fluted portion comprising a non-threaded body comprising a flute, the flute configured to create a hole in the bone;
   a threaded portion rigidly coupled to and proximate the bit portion, wherein the fluted portion extends into the threaded portion such that threads of the threaded portion include at least one broken section; and
   a conduit, the conduit extending entirely through the luer portion and the bit portion, and the conduit extending at least partially through the fluted portion;

wherein the flute extends from the non-threaded body away from the conduit and defines an aperture, the aperture extending from the conduit entirely through the flute, and the aperture is configured to allow the substance to pass therethrough, and wherein the flute includes a plurality of grooves extending from the aperture to facilitate flow of the substance from the aperture to the bone.

16. A device for delivering substance to bone, comprising:

a luer portion configured to be detachably coupled to a bit driver, the luer portion comprising a luer thread;

a bit portion rigidly coupled to the luer portion, the bit portion configured to accommodate the bit driver;

a fluted portion rigidly coupled to the bit portion, the fluted portion comprising a non-threaded body comprising a flute, the flute configured to create a hole in the bone, wherein the flute extends circumferentially around a portion of a circumference of the fluted portion; and a conduit, the conduit extending entirely through the luer portion and the bit portion, and the conduit extending at least partially through the fluted portion;

wherein the flute extends from the non-threaded body away from the conduit and defines an aperture, the aperture extending from the conduit entirely through the flute, and the aperture is configured to allow the substance to pass therethrough, and wherein the flute includes a plurality of grooves extending from the aperture to facilitate flow of the substance from the aperture to the bone.

* * * * *